United States Patent [19]

Degner et al.

[11] Patent Number: 4,759,832
[45] Date of Patent: * Jul. 26, 1988

[54] PREPARATION OF BISCARBAMATES AND NOVEL BISCARBAMATES

[75] Inventors: Dieter Degner, Dannstadt-Schauernhein; Heinz Hannebaum, Ludwigshafen, both of Fed. Rep. of Germany

[73] Assignee: BASF Aktiengesellschaft, Rhienland-Pfalz, Fed. Rep. of Germany

[*] Notice: The portion of the term of this patent subsequent to Apr. 28, 2004 has been disclaimed.

[21] Appl. No.: 14,635

[22] Filed: Feb. 13, 1987

[30] Foreign Application Priority Data

Feb. 28, 1986 [DE] Fed. Rep. of Germany ....... 3606478

[51] Int. Cl.$^4$ .............................................. C25B 3/02
[52] U.S. Cl. .................................... 204/59 R; 204/72; 560/115
[58] Field of Search ............. 560/158, 115; 204/59 R, 204/72, 73

[56] References Cited

U.S. PATENT DOCUMENTS

| | | | |
|---|---|---|---|
| 3,226,428 | 12/1965 | Vail et al. | 560/158 |
| 3,341,568 | 9/1967 | Ham | 560/158 |
| 3,391,181 | 7/1968 | Scheuerl | 560/158 |
| 3,950,285 | 4/1976 | Wolgemuth | 560/158 |
| 4,118,500 | 10/1978 | Mitzlaff et al. | 204/59 R |
| 4,430,262 | 2/1984 | Engels et al. | 204/59 R |
| 4,661,217 | 4/1987 | Degner et al. | 204/59 R |

OTHER PUBLICATIONS

Tetrahedron 32 (1976), 2815-2206.
Journal of Organic Chemistry 48 (1983) 3338-3339.

*Primary Examiner*—John F. Niebling
*Assistant Examiner*—Steven P. Marquis
*Attorney, Agent, or Firm*—John H. Shurtleff

[57] ABSTRACT

Biscarbamates, including novel one, of the general formula

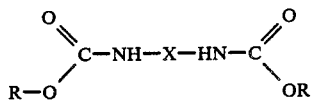

I where R is alkyl of 1 to 8 carbon atoms and X is a hydrocarbon radical of 2 to 60 carbon atoms in which one or more carbon atoms may be replaced by hetero atoms and which may contain halogen atoms or ester, carbonyl or nitrile groups are prepared by electrochemically oxidizing formamides of the general formula

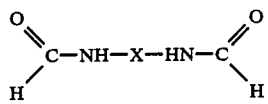

II in the presence of an alkanol of the formula ROH and of an ionic halide.

5 Claims, No Drawings

PREPARATION OF BISCARBAMATES AND NOVEL BISCARBAMATES

The present invention relates to a novel process for preparing biscarbamates and to novel biscarbamates.

It is known to prepare carbamates by reaction of alcohols with phosgene to give chloroformates and subsequent aminolysis. Handling the highly toxic and corrosive and starting material intermediates necessitates an appreciable engineering out-lay. Furthermore, these processes give rise to hydrochloric acid or halogen-containing waste salts which are frequently very difficult to separate off (Ullmann, Enzyklopädie der techn. Chemie, 4th edition, Volume 9, pages 118–119).

In a phosgene-free method of preparation, urea is reacted with an alkanol. The disadvantages of this method are the high reaction temperature, the long reaction time and the technically complicated handling of solids (Houben-Weyl, Methoden der organischen Chemie, 1952, Volume 8, page 140).

It is an object of the present invention to provide a process which makes it possible to prepare biscarbamates in a technically simple and environmentally particularly safe manner.

We have found that this object is achieved with a process wherein a biscarbamate of the general formula

    I where R is alkyl of 1 to 8 carbon atoms and X is a hydrocarbon radical of 2 to 60 carbon atoms in which one or more carbon atoms may be replaced by hetero atoms and which may contain halogen atoms or ester, carbonyl or nitrile groups, by electrochemically oxidizing a formamide of the general formula

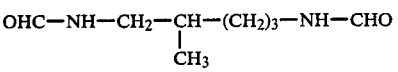
    II where X has the abovementioned meaning, in the presence of an alkanol of the formula ROH, where R has the abovementioned meaning, and of an ionic halide.

This process also relates to the novel biscarbamate of the formula

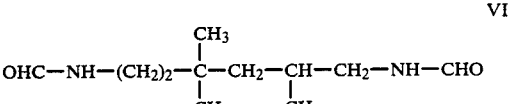
    III where $R^1$ is alkyl of 1 to 4 carbon atoms and Y is one of the following radicals:

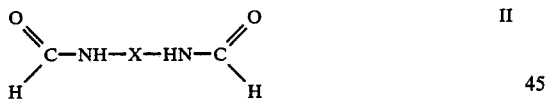

$-(CH_2)_3-O-(CH_2)_4-O-(CH_2)_3-$

-continued
$-(CH_2)_3-O-(CH_2)_2-O-(CH_2)_2-O-(CH_2)_3-$

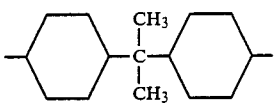

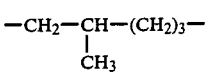

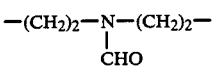

In the starting material for preparing the biscarbamate of the formula I, namely the formamide of the formula II, the divalent radical X is a straight-chain, branched or annular hydrocarbon radical of 2 to 60, preferably 3 to 30, in particular 3 to 12, carbon atoms, such as alkyl, cycloalkyl or alkylaryl. In these hydrocarbon radicals, one or more carbon atoms may be replaced by hetero atoms, such as N, O or S. The hydrocarbon radicals mentioned may also carry halogen atoms or ester, carbonyl or nitrile groups.

Examples are the following formamides:

$OHC-NH-(CH_2)_n-NHCHO$     IV where n is 3 to 30

$OHC-NH-CH_2-CH(CH_3)-(CH_2)_3-NH-CHO$     V

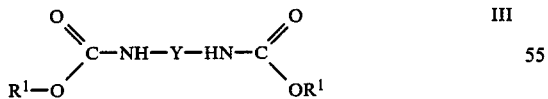     VI

     VII

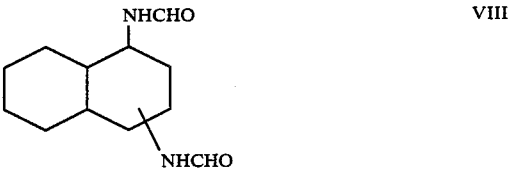     VIII

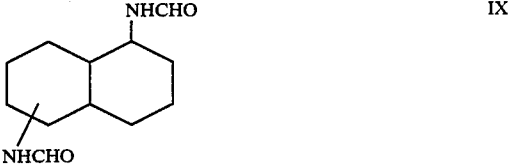     IX

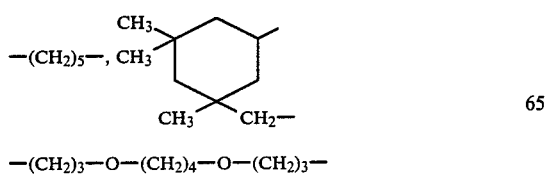     X

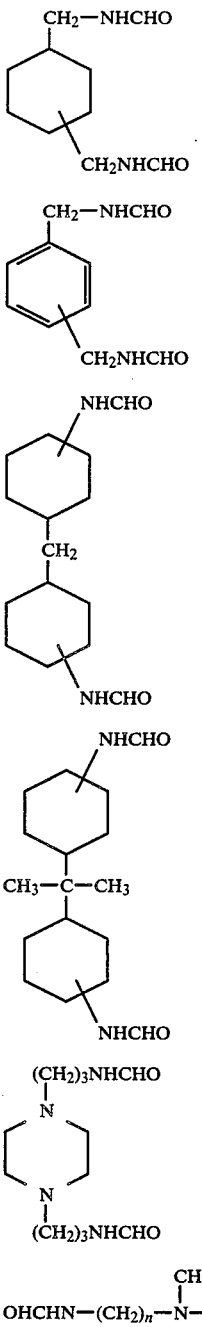

XI

XII

XIII

XIV

XV

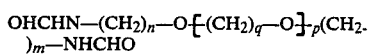
XVI where n and m are each 2 to 30

OHCHN—(CH$_2$)$_n$—O—[(CH$_2$)$_q$—O]$_p$(CH$_2$)$_m$—NHCHO  XVII where n, m and q are each 2 to 30 and p is 1 to 4

In the alcohol of the formula ROH, R is alkyl of 1 to 8, preferably 1 to 5, in particular 1 to 4, carbon atoms. Examples of alkanols are n- or i-propanol, n-butanol, but in particular methanol and ethanol.

Suitable ionic halides are salts, such as the alkali metal, alkaline earth metal or ammonium salts of hydriodic, hydrobromic or hydrochloric acid. Particular preference is given to salts of hydrobromic acid, such as alkali metal and alkaline earth metal bromides as well as quaternary ammonium bromides, in particular tetraalkylammonium bromides. The cation does not play an essential part in the invention, and therefore it is also possible to use other ionic metal halides. It is expedient to choose inexpensive halides. Examples are sodium bromide, potassium bromide, calcium bromide, ammonium bromide and di-, tri- and tetramethyl- or tetraethyl-ammonium bromide.

The process according to the invention does not require a special electrolysis cell. Advantageously it can be carried out in an undivided continuous flow cell. The anode may be made of any conventional anode material which is stable under the electrolysis conditions, such as a noble metal, for example gold or platinum. The preferred anode material is graphite. The cathode material comprises for example a metal, such as lead, iron, steel, nickel or a noble metal such as platinum. The preferred cathode material is likewise graphite.

The composition of the electrolyte can be varied within wide limits. The electrolyte contains for example the starting materials in the following weight ratios:

1–50% by weight of formamide of the formula II
40–90% by weight of alkanol
0.1–10% by weight of halide.

To the electrolyte may be added, if desired, a solvent, for example for improving the solubility of the formamide or of the halide. Suitable solvents are nitriles, such as acetonitrile, carbonates, such as dimethyl carbonate, ethers, such as tetrahydrofuran, and dialkylformamides such as dimethylformamide. The current density is not a limiting factor in the process according to the invention, ranging for example from 1 to 25 A/dm$^2$, preferably from 3 to 12 A/dm$^2$. The electrolysis is carried out for example at up to 120° C. If the electrolysis is carried out at atmospheric pressure, the upper limit of the temperature range chosen is expediently not less than 5°–10° C. below the boiling point of the electrolyte. If methanol or ethanol is used, the electrolysis is preferably carried out at 20°–50° C.

The electrolyzed mixture can be worked up in a conventional manner. Expediently the electrolyzed mixture is initially worked up by distillation. Excess alkanol and any cosolvent used are distilled off. The halide is separated off in a conventional manner, for example by filtration or extraction. The biscarbamate is thereafter frequently obtained in a very pure form; if necessary it can be purified further, for example by reprecipitation or recrystallization. Alkanol, any still unconverted formamide, cosolvent and halide can be recycled for electrolysis. The process according to the invention can be carried out not only batchwise but also continuously.

The process according to the invention produces biscarbamates in a particularly advantageous manner. The novel process makes it possible, surprisingly, to obtain substantial formamide conversions without impairing the yield. Even the electric current yields are remarkably high with the process according to the invention. For instance, complete conversion of the formamide is usually achieved with 4–5 F/mol of formamide. These favorable results were not to be expected, since it has been known for a long time that the electrochemical conversion of formamides in alcohols in the presence of conducting salts such as tetraalkylammonium tetrafluoroborate leads to alkoxyformamides (see Tetrahedron 32 (1976), 2815–2206) and that under electrolysis conditions and using conducting salts such as tetraethylammonium p-toluenesulfonate, biscarbamates are electrochemically further oxidized (see J. Org. Chem. 48 (1983), 3338-3339).

Biscarbamates are versatile intermediates for the synthesis of isocyanates. The novel biscarbamates serve in particular for preparing specific polyurethanes.

EXAMPLE 1

Electrosynthesis of
CH₃OOCHN—(CH₂)₆NHCOOCH₃

| Apparatus: | undivided cell with 11 electrodes |
|---|---|
| Anode: | graphite |
| Electrolyte: | 300 g of formamide of the formula IV where n = 6 (8.5% by weight) |
| | 36 g of NaBr (1.0% by weight) |
| | 3204 g of CH₃OH (90.5% by weight) |
| Cathode: | graphite |
| Current density: | 3.3 A/dm² |
| Temperature: | 25° C. |
| Electrolysis with | 5.3 F/mol of formamide |
| Flowrate through cell: | 200 l/h |

Workup:

On completion of the electrolysis, methanol is distilled off under atmospheric pressure, and the residue is dissolved in methyl ethyl ketone by heating. The sodium bromide (36 g) is filtered off hot. The reaction product is recrystallized from the filtrate, giving 385 g of CH₃OOC—NH—(CH₂)₆—NHCOOCH₃ (melting point 112° C., pure by ¹H—NMR spectrum; analysis for C₁₀H₂₀N₂O₄ (%); calculated: C 51.7, H 8.6, O 27.6, N 12.1; found: C 51.7, H 8.5, O 27.6, N 12.0). This corresponds to a yield of 95.1%.

EXAMPLE 2

Electrosynthesis of
CH₃OCONH—(CH₂)₄NHCOOCH₃

| Apparatus: | undivided cell with 6 electrodes |
|---|---|
| Anode: | graphite |
| Electrolyte: | 300 g of formamide of the formula IV where n = 4 (10.0% by weight) |
| | 30 g of NaBr (1.0% by weight) |
| | 2670 g of CH₃OH (89.0% by weight) |
| Cathode: | graphite |
| Current density: | 3.3 A/dm² |
| Temperature: | 25° C. |
| Electrolysis with | 4.75 F/mol of formamide |
| Flowrate through cell: | 200 l/h |

Workup:

The workup of Example 1 is repeated, affording in addition to 27 g of sodium bromide 356 g of CH₃O-CONH—(CH₂)₄—NHCOOCH₃ (melting point 126°-128° C., pure by ¹H—NMR spectrum). This corresponds to a yield of 83.8%.

EXAMPLE 3

Electrosynthesis of
CH₃OCONH—(CH₂)₅—NHCOOCH₃

| Apparatus: | undivided cell with 6 graphite electrodes |
|---|---|
| Anode: | graphite |
| Electrolyte: | 140 g of formamide of the formula IV where n = 5 (4.7% by weight) |
| | 30 g of NaBr (1.0% by weight) |
| | 2830 g of CH₃OH (94.3% by weight) |
| Cathode: | graphite |

| Current density: | 3.3 A/dm² |
|---|---|
| Temperature: | 25° C. |
| Electrolysis with | 4.4 F/mol of formamide |
| Flowrate through cell: | 200 l/h |

Workup:

The workup of Example 1 is repeated, affording in addition to 30 g of sodium bromide 175 g of CH₃O-CONH—(CH₂)₅—NHCOOCH₃ (melting point 104°-112° C., pure by ¹H—NMR spectrum; analysis calculated for C₉H₁₈N₂O₄ (%); calculated C 49.5, H 8.3, O 29.4, N 12.8; found C 49.5, H 8.1, O 29.4, N 12.8). This corresponds to a yield of 90.6%.

EXAMPLE 4

Electrosynthesis of 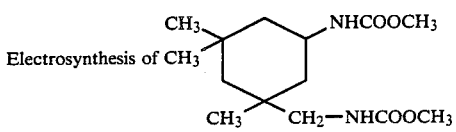

| Apparatus: | undivided cell with 11 electrodes |
|---|---|
| Anode: | graphite |
| Electrolyte: | 279.2 g of formamide of the formula X (8.8% by weight) |
| | 32 g of NaBr (1.0% by weight) |
| | 2848 g of CH₃OH (90.2% by weight) |
| Cathode: | graphite |
| Current density: | 3.3 A/dm² |
| Temperature: | 20-22° C. |
| Electrolysis with | 4.5 F/mol of formamide |
| Flowrate through cell: | 200 l/h |

Workup:

On completion of the electrolysis, methanol is distilled off under atmospheric pressure. The solid residue is taken up in methyl ethyl ketone, and the undissolved solid (32 g, NaBr) is filtered off. Methyl ethyl ketone is distilled out of the filtrate. The residue is recrystallized from a little methyl ethyl ketone. This gives 282 g of the biscarbamate (melting point 103°-117° C.; pure according to ¹H—NMR and ¹³C—NMR spectra; cis-trans mixture). This corresponds to a yield of 79.8%.

EXAMPLE 5

Electrosynthesis of

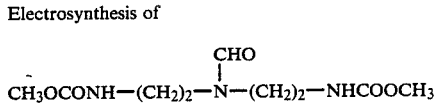

| Apparatus: | undivided cell with 11 electrodes |
|---|---|
| Anode: | graphite |
| Electrolyte: | 330 g of formamide of the formula XVI where n = m = 2 (10% by weight) |
| | 33 g of NaBr (1% by weight) |
| | 2937 g of CH₃OH (89% by weight) |
| Cathode: | graphite |
| Current density: | 3.3 A/dm² |
| Temperature: | 25° C. |
| Electrolysis with | 4.5 F/mol of formamide |
| Flowrate through cell: | 200 l/h |

Workup:

On completion of the electrolysis, methanol is distilled off at room temperature. The residue is taken up in methylene chloride, and sodium bromide (28 g) is filtered off. Methylene chloride is distilled out of the filtrate. The residue left behind (408 g) is then recrystallized from methyl ethyl ketone. This gives 248.2 g of biscarbamate (melting point 90°-92° C.; pure by $^1$H—NMR and $^{13}$C—NMR spectra; analysis for $C_9H_{17}N_3O_5$ calculated (%): C 43.7, H 6.9, O 32.4, N 17.0; found C 43.6, H 6.8, O 32.1, N 17.1). The mother liquor yields a further 128.5 g of the biscarbamate. This corresponds to a total yield of 86.4%.

EXAMPLE 6

Electrosynthesis of
$CH_3OOCHN—(CH_2)_3—O—(CH_2)_4—O—(CH_2)_3—NHCOOCH_3$

| Apparatus: | undivided cell with 11 electrodes |
|---|---|
| Anode: | graphite |
| Electrolyte: | 330 g of formamide of the formula XVII where n = m = 3, q = 4, p = 1 (10% by weight) |
| | 33 g of NaBr (1% by weight). |
| | 2937 g of $CH_3OH$ (89% by weight) |
| Cathode: | graphite |
| Current density: | 3.3 A/dm$^2$ |
| Temperature: | 25° C. |
| Electrolysis with | 4.75 F/mol of formamide |
| Flowrate through cell: | 200 l/h |

Workup:

On completion of the electrolysis, methanol is distilled off under atmospheric pressure. The residue is taken up in methyl ethyl ketone, sodium bromide is then filtered off (32 g), and methyl ethyl ketone is distilled off. This gives 357 g of $CH_3OCONH—(CH_2)_3—O—(CH_2)_4—O—(CH_2)_3—NHCOOCH_3$ (melting point 45°-46° C.; pure by $^1$H—NMR and $^{13}$C—NMR spectra; analysis calculated for $C_{14}H_{28}N_2O_6$ (%): C 52.5, H 8.8, O 30.0, N 8.8; found: C 52.7, H 8.7, O 29.6, N 8.8.). This corresponds to a yield of 87.9%.

EXAMPLE 7

Electrosynthesis of
$CH_3OCONH—(CH_2)_3—O—[(CH_2)_2—O]_2—(CH_2)_3—NHCOOCH_3$

| Apparatus | undivided cell with 6 electrodes |
|---|---|
| Anode: | graphite |
| Electrolyte: | 260 g of formamide of the formula XVII where n = m = 3, q = 2, p = 2 (10% by weight) |
| | 26 g of NaBr (1% by weight) |
| | 2314 g of $CH_3OH$ (89% by weight) |
| Cathode: | graphite |
| Current density: | 3.3 A/dm$^2$ |
| Temperature: | 20-22° C. |
| Electrolysis with | 4.75 F/mol of formamide |
| Flowrate through cell: | 200 l/h |

Workup:

On completion of the electrolysis, methanol is distilled off under atmospheric pressure. The residue is taken up in toluene, sodium bromide is then filtered off (22 g), and toluene is distilled off again. This gives 275 g of $CH_3OOCNH(CH_2)_3—O—(CH_2)_2—O—(CH_2)_2—O—(CH_2)_3NHCOOCH_3$ (viscous oil, pure by $^1$H—NMR and $^{13}$C—NMR spectra; analysis for $C_{14}H_{28}N_2O_7$ calculated (%): C 50.0, H 8.3, O 33.4, N 8.3; found: C 50.2, H 8.2, O 33.3, N 8.5). This corresponds to a yield of 86.9%.

EXAMPLE 8

Electrosynthesis of

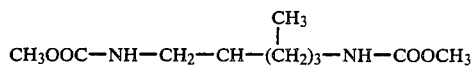

$$CH_3OOC—NH—CH_2—CH(CH_3)—(CH_2)_3—NH—COOCH_3$$

| Apparatus: | undivided cell with 6 electrodes |
|---|---|
| Anode: | graphite |
| Electrolyte: | 260 g of formamide of the formula V (10% by weight) |
| | 26 g of NaBr (1% by weight) |
| | 2314 g of $CH_3OH$ (89% by weight) |
| Cathode: | graphite |
| Current density: | 3.3 A/dm$^2$ |
| Temperature: | 27° C. |
| Electrolysis with | 4.5 F/mol of formamide |
| Flowrate through cell: | 200 l/h |

Workup:

On completion of the electrolysis, methanol is distilled off under atmospheric pressure. The residue is taken up in methyl tert.-butyl ether, and sodium bromide (24 g) is filtered off. Methyl tert.-butyl ether is distilled out of the filtrate. This gives 290 g of $CH_3OOC—NH—CH_2—CH(CH_3)—(CH_2)_3—NHCOOCH_3$ (yellow liquid, pure by $^1$H—NMR and $^{13}$C—NMR spectra; analysis for $C_{10}H_{20}N_4O_2$ (%): C 51.7, H 8.6, O 27.6, N 12.1; found: C 51.7, H 8.7, O 27.7, N 12.5). This corresponds to a yield of 82.7%.

EXAMPLE 9

Electrosynthesis of

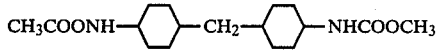

| Apparatus: | undivided cell with 6 electrodes |
|---|---|
| Anode: | graphite |
| Electrolyte: | 86 g of |

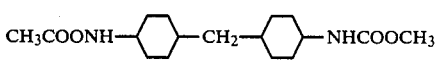

| | (3.5% by weight) |
| | 26 g of NaBr |
| | (1.1% by weight) |
| | 2314 g of $CH_3OH$ |
| | (95.4% by weight) |
| Cathode: | graphite |
| Current density: | 3.3 A/dm$^2$ |
| Temperature: | 43-50° C. |
| Electrolysis with | 4.5 F/mol of formamide |
| Flowrate through cell: | 200 L/h |

Workup:

On completion of the electrolysis, the electrolyte is cooled down to 10° C. to precipitate 38.4 g of

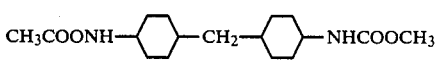

(melting point 195°–200° C., cis-trans mixture pure by $^1$H—NMR and $^{13}$C—NMR spectra). Methanol is then distilled off under atmospheric pressure, the residue is taken up in CH$_2$CL$_2$, NaBr (24.5 g) is filtered off, and CH$_2$CL$_2$ is distilled off. This gives a further 51 g of the biscarbamate (melting point 168°–173° C.). This corresponds to a total yield of 84.8%.

EXAMPLE 10

Electrosynthesis of

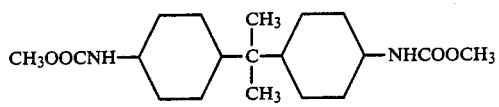

| Apparatus: | undivided cell with 6 electrodes |
|---|---|
| Anode: | graphite |
| Electrolyte: | 260 g of |

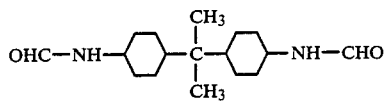

| | (10% by weight) |
|---|---|
| | 26 g of NaBr |
| | (1% by weight) |
| | 2314 g of CH$_3$OH |
| | (89% by weight) |
| Cathode: | graphite |
| Current density: | 3.3 A/dm$^2$ |
| Temperature: | 27° C. |
| Electrolysis with | 4.0 F/mol of formamide |
| Flowrate through cell: | 200 L/h |

Workup:

On completion of the electrolysis, methanol is distilled off under atmospheric pressure. The residue is dissolved in diethyl ketone and washed with water. The organic phase is dried with sodium sulfate, and diethyl ketone is then distilled off. This gives 206.7 g of the biscarbamate of the formula shown above (melting point 137°–145° C., cis-trans mixture pure by $^1$H—NMR and $^{13}$C—NMR spectra; analysis calculated for C$_{19}$H$_{34}$O$_4$N$_2$ (%): C 64.4, H 9.6, O 18.1, N 7.9; found: C 64.3, H 9.8, O 18.0, N 7.9). This corresponds to a yield of 66%.

EXAMPLE 11

Electrosynthesis of

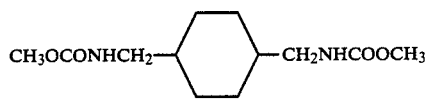

| Apparatus: | undivided cell with 6 electrodes |
|---|---|
| Anode: | graphite |
| Electrolyte: | 31.6 g of |

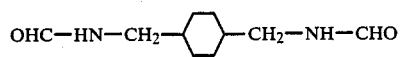

| | (1.3% by weight) |
|---|---|
| | 26 g of NaBr |
| | (1.1% by weight) |
| | 2314 g of CH$_3$OH |
| | (97.6% by weight) |
| Cathode: | graphite |
| Current density: | 3.3 A/dm$^2$ |
| Temperature: | 25–27° C. |
| Electrolysis with | 4.5 F/mol of formamide |
| Flowrate through cell: | 200 L/h |

Workup:

On completion of the electrolysis, methanol is distilled off under atmospheric pressure. The residue is taken up in methylene chloride. Sodium bromide (25 g) is filtered off, and methylene chloride is distilled off. This gives 29.9 g of the biscarbamate of the formula shown above (melting range 144°–167° C., cis-trans mixture pure by $^1$H—NMR and $^{13}$C—NMR spectra; analysis calculated for C$_{12}$H$_{22}$N$_2$O$_4$ (%): C 55.8, H 8.6, O 24.8, N 10.8; found: C 55.7, H 8.5, O 24.8, N 10.9). This corresponds to a yield of 72.6%.

EXAMPLE 12

Electrosynthesis of

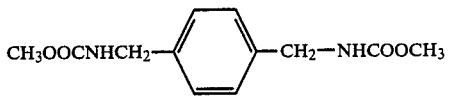

| Apparatus: | undivided cell with 6 electrodes |
|---|---|
| Anode: | graphite |
| Electrolyte: | 80 g of |

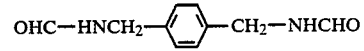

| | (3.0% by weight) |
|---|---|
| | 26 g of NaBr |
| | (1.0% by weight) |
| | 1357 g of (CH$_3$)$_2$NCHO |
| | (51.8% by weight) |
| | 1157 g of CH$_3$OH |
| | (44.2% by weight) |
| Cathode: | graphite |
| Current density: | 3.3 A/dm$^2$ |
| Temperature: | 27° C. |
| Electrolysis with | 6.6 F/mol of formamide |
| Flowrate through cell: | 200 L/h |

Workup:

On completion of the electrolysis, first methanol is distilled off under atmospheric pressure and then dimethylformamide is distilled off under a column top pressure of 15 mbar at up to 110° C. (column bottom temperature). The residue is triturated with water at 80° C., which is followed by filtration and drying. This gives 81 g of the biscarbamate of the formula shown above (melting point 186° C., pure by $^1$H—NMR and $^{13}$C—NMR spectra; analysis calculated for C$_{12}$H$_{16}$N$_2$O$_4$ (%): C 57.1, H 6.4, O 25.4, N 11.1; found: C 57.0, H 6.4, O 25.3, N 11.0). This corresponds to a yield of 77.1%.

We claim:

1. A process for preparing a biscarbamate of the general formula cally oxidizing a formamide of the general formula

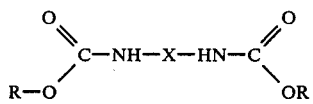

where R is alkyl of 1 to 8 carbon atoms and X is a hydrocarbon radical of 2 to 60 carbon atoms in which one or more carbon atoms may be replaced by hetero atoms and which may contain halogen atoms or ester, carbonyl or nitrile groups, which comprises electrochemically oxidizing a formamide of the general formula

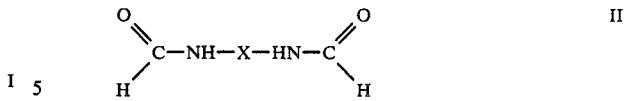

where X has the abovementioned meaning, in the presence of an alkanol of the formula ROH, where R has the abovementioned meaning, and of an ionic halide.

2. A process as claimed in claim 1, wherein the ionic halide used is a salt of hydrobromic acid.

3. A process as claimed in claim 1, wherein the anode used for the electrochemical oxidation is made of graphite.

4. A process as claimed in claim 1, wherein the alkanol used is methanol.

5. A process as claimed in claim 1, wherein the electrochemical oxidation is carried out on an electrolyte which contains 1–50% by weight of formamide of the formula II, 40–90% by weight of alkanol of the formula ROH and 0.1–10% by weight of ionic halide.

* * * * *